(12) United States Patent
Baumann et al.

(10) Patent No.: US 11,529,196 B2
(45) Date of Patent: Dec. 20, 2022

(54) INSTRUMENT GUIDING DEVICE

(71) Applicant: KOELIS, Meylan (FR)

(72) Inventors: Michael Baumann, Grenoble (FR); Eric Gaudard, Lyons (FR); Antoine Leroy, Bois D'Arcy (FR); Paul Mignon, Lyons (FR); Patrick Henri, Bois Colombes (FR)

(73) Assignee: KOELIS, Meylan (FR)

( * ) Notice: Subject to any disclaimer, the term of this patent is extended or adjusted under 35 U.S.C. 154(b) by 457 days.

(21) Appl. No.: 16/648,563

(22) PCT Filed: Sep. 20, 2018

(86) PCT No.: PCT/EP2018/075505
§ 371 (c)(1),
(2) Date: Mar. 18, 2020

(87) PCT Pub. No.: WO2019/057833
PCT Pub. Date: Mar. 28, 2019

(65) Prior Publication Data
US 2020/0214768 A1 Jul. 9, 2020

(30) Foreign Application Priority Data

Sep. 22, 2017 (FR) ...................... 1758795

(51) Int. Cl.
*A61B 34/20* (2016.01)
*A61B 90/11* (2016.01)
(Continued)

(52) U.S. Cl.
CPC .............. *A61B 34/20* (2016.02); *A61B 90/11* (2016.02); *A61B 2017/00119* (2013.01);
(Continued)

(58) Field of Classification Search
None
See application file for complete search history.

(56) References Cited

U.S. PATENT DOCUMENTS 6,256,529 B1 7/2001 Holupka et al.
6,733,458 B1 5/2004 Steins et al.
(Continued)

FOREIGN PATENT DOCUMENTS

WO 2007/095637 A1 8/2007
WO 2016/184746 A1 11/2016

*Primary Examiner* — Saptarshi Mazumder
(74) *Attorney, Agent, or Firm* — Sughrue Mion, PLLC

(57) ABSTRACT

The invention relates to a medical instrument guiding device comprising the medical instrument, a monitoring device (2) comprising a support (3) and a medical imaging probe (4) which is arranged on the support, a screen (10), and a control unit (11) of the device which is connected to the screen and the probe for generating at least one three-dimensional image, the control unit being configured to generate at least one two-dimensional image on the screen showing a deformation of the instrument from at least the three-dimensional image, the control unit being configured to estimate a virtual path of the instrument from the deformation of the instrument for extending the insertion thereof to a target, and deduce therefrom at least one distance between the virtual path and the target.

15 Claims, 8 Drawing Sheets

(51) Int. Cl.
　　　*A61B 34/10*　　　　(2016.01)
　　　*A61B 90/00*　　　　(2016.01)
　　　*A61B 17/00*　　　　(2006.01)
　　　*A61B 17/34*　　　　(2006.01)

(52) U.S. Cl.
　　　CPC ............... *A61B 2017/00199* (2013.01); *A61B 2017/3413* (2013.01); *A61B 2034/107* (2016.02); *A61B 2034/2063* (2016.02); *A61B 2034/2065* (2016.02); *A61B 2090/378* (2016.02)

(56) References Cited

U.S. PATENT DOCUMENTS

| | | | |
|---|---|---|---|
| 2001/0029334 A1* | 10/2001 | Graumann | A61B 8/4254 378/4 |
| 2011/0234780 A1 | 9/2011 | Ito et al. | |
| 2013/0211244 A1* | 8/2013 | Nathaniel | A61B 5/7264 600/424 |
| 2013/0216025 A1* | 8/2013 | Chan | A61B 6/54 378/63 |
| 2018/0132944 A1* | 5/2018 | Yan | G06T 7/73 |

\* cited by examiner

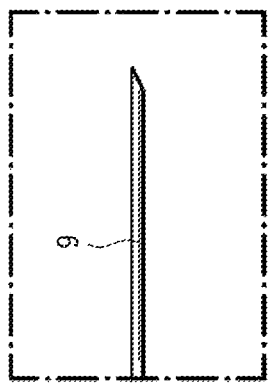
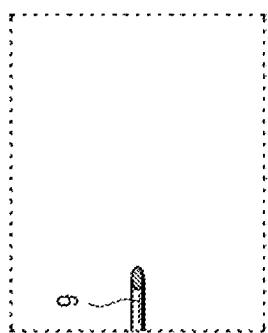
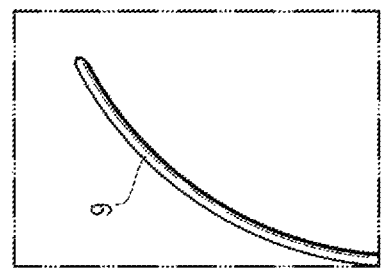
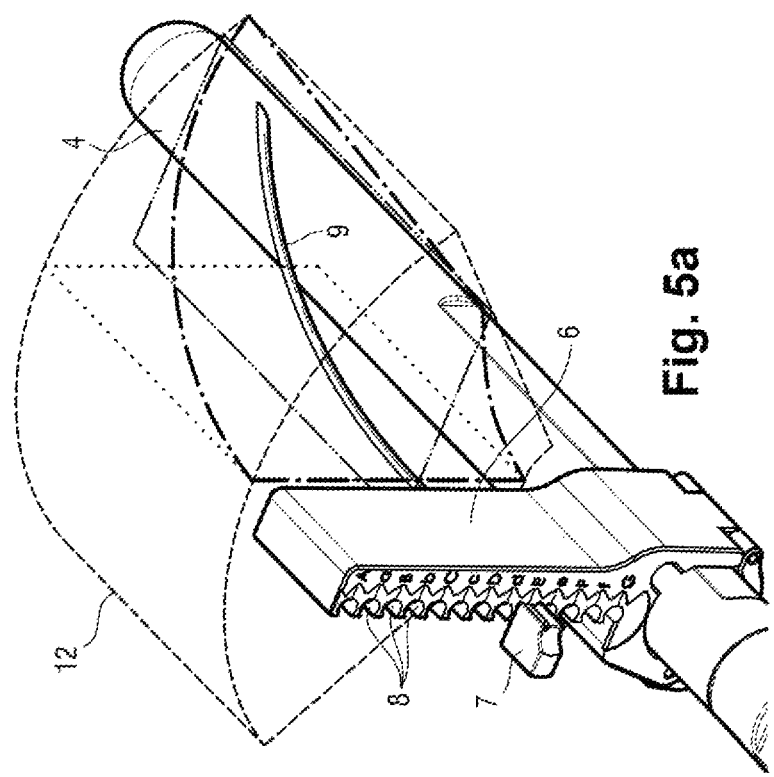

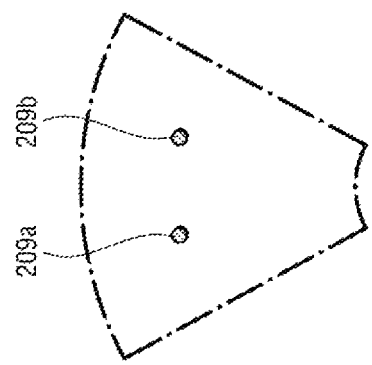
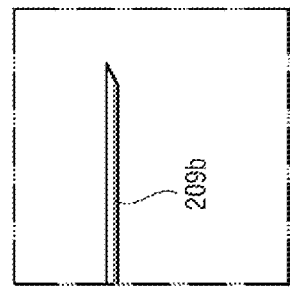
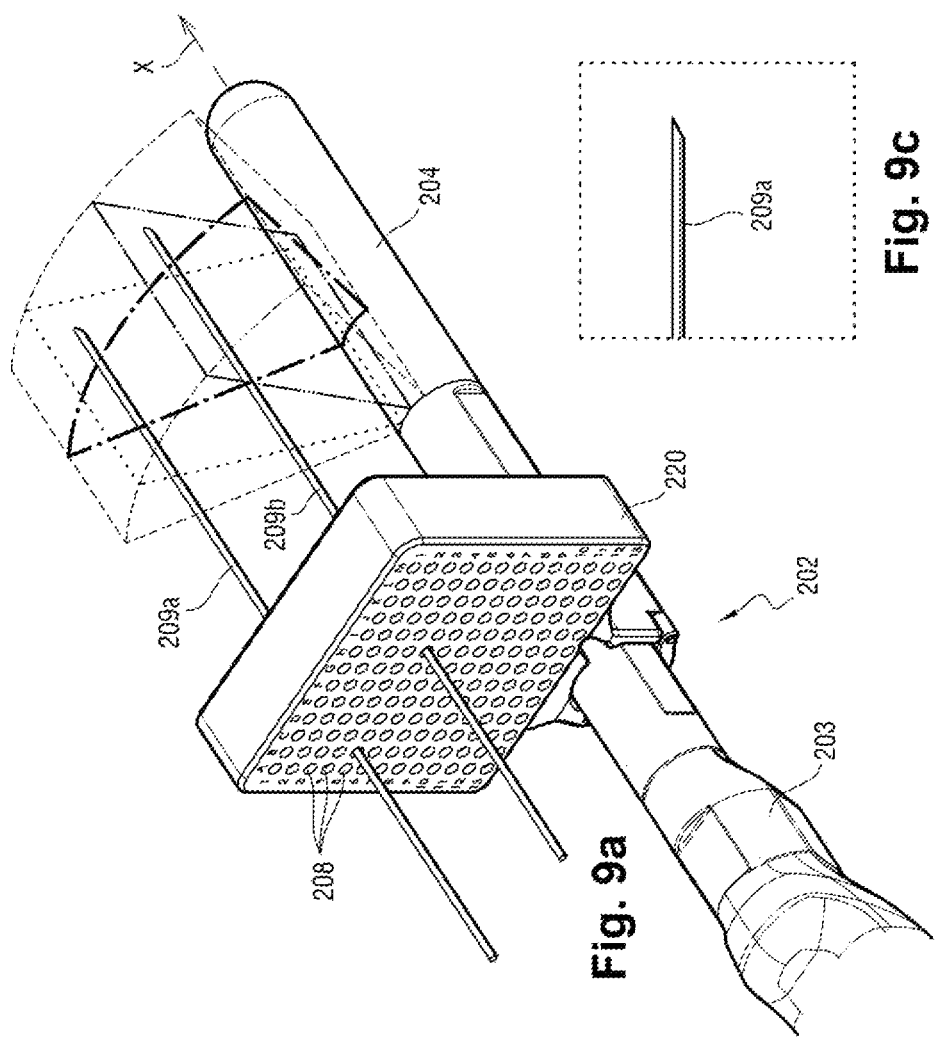

INSTRUMENT GUIDING DEVICE

CROSS REFERENCE TO RELATED APPLICATIONS

This application is a National Stage of International Application No. PCT/EP2018/075505 filed Sep. 20, 2018, claiming priority based on French Patent Application No. 1758795 filed Sep. 22, 2017.

The invention relates to a device for guiding an instrument. The invention also relates to a corresponding method.

BACKGROUND ART

Many operations involve inserting an instrument into the body of the patient through a natural or artificial opening. This is the case, for example, in a biopsy with insertion of a needle (for collecting samples), in brachytherapy with insertion of a catheter (for positioning radioactive seeds) or in other targeted treatments such as cryotherapy or laser therapy.

A medical imaging system is thus normally assigned to the instrument in order to monitor the position of the latter in the body of the patient.

In the case of a biopsy of the prostate, a device is thus known comprising a needle holder combined with a medical imaging probe.

In the case of a transrectal approach, the needle holder is rigidly connected to the probe and is introduced with the latter into the rectum of the patient. The needle holder thus has only a single opening through which to guide the biopsy needle when the needle holder is in place against the prostate.

It therefore proves relatively simple for an operator to direct the needle correctly, especially since the needle holder is in immediate proximity to the prostate.

By contrast, in a transperineal approach, the needle proves much more difficult to guide. The reason is that, with this approach, it is only the probe that is introduced into the rectum: the needle holder remains outside the patient, placed against the skin of the perineum of the patient. The needle therefore has a greater path to travel, which makes steering the needle more complex.

OBJECT OF THE INVENTION

It is an object of the invention to make available a guiding device that makes it easier to steer an instrument relative to a patient.

It is an object of the invention also to make available a corresponding method.

BRIEF DESCRIPTION OF THE INVENTION

In order to achieve this object, a device for guiding a medical instrument is proposed, comprising:
the medical instrument,
a monitoring appliance having a support and a medical imaging probe, which is arranged on the support and which is intended to be positioned in proximity to at least one target present in or on the patient,
a screen, and
a control unit which controls the device and which is connected to the screen and to the probe in order to generate at least one three-dimensional image, the control unit being configured to generate on the screen, from at least said three-dimensional image, at least one two-dimensional image showing a deformation of the instrument,
the control unit being configured to estimate, from this deformation of the instrument, a virtual path of the instrument if the insertion thereof were continued as far as the target, and to deduce therefrom at least one distance between said virtual path and the target.

Thus, by acquiring images of the instrument, it is easier to guide the instrument, particularly if the instrument has moved relative to the intended position of application of the instrument on the target.

Thus, when the operator sees on the screen that the instrument has deformed, he can stop the maneuver. Depending on the result from the control unit concerning the distance between the virtual path and the target, the operator can then withdraw the instrument, in order to better position it, or can continue the maneuver, possibly by adjusting and correcting the trajectory of the instrument if possible.

The invention thus proves particularly effective in helping to position an instrument relative to a target.

In particular, without the invention, the clinician would be able to withdraw the instrument when he could easily have reached the target. Worse, he could continue his maneuver fully in the hope of reaching the target but without succeeding.

The invention thus makes it possible to optimize the insertions and to reduce the duration of the intervention. Moreover, there is thus less risk of moving the instrument into unsuitable locations. Taking the example of a prostate biopsy, the invention limits the risk of the bladder being punctured through poor placement of the needle.

In the case of a biopsy, the risks of infection and bleeding are also reduced.

The invention thus offers an operator the possibility of displaying not only a three-dimensional image of the anatomical volume on which to operate, but also two-dimensional images, of which at least one is able to display, if necessary, the deformation of the instrument.

This allows an operator to more easily visualize the relationship between the instrument and the target volume and thus to intervene more effectively on the target. In addition, the two-dimensional image is generated by working on the three-dimensional image, which makes it possible not to have to move the support.

Furthermore, it is thus possible to display on the screen images that are not accessible directly by the probe, for example a two-dimensional image comprising a projection of the instrument.

A "deformation of the instrument" is here understood both as an unintentional deformation of the instrument and as an intentional deformation of the instrument (that is to say a deformation that is wanted for reasons relating to surgical techniques), and also as a permanent deformation of the instrument, for example in the case where the instrument does not extend in a substantially rectilinear direction (for example the instrument is curved), it being understood that such an instrument can then have an intentional or unintentional additional deformation during its movement relative to the target. Moreover, the deformation can equally well be of a curved or oblique nature (then causing a deviation of the instrument).

In particular, the invention can thus be used for a biopsy by a transperineal approach, ensuring a good guiding of the instrument.

A target is here understood to mean both a zone outside the patient and a zone inside the patient. By way of non-limiting examples, the target can thus be:

- a tumor or any other zone of the body of the patient that is considered to be malignant or suspicious;
- an anatomical volume such as an organ, for example the kidney, breast, uterus, thyroid, liver, bladder, urethra or prostate, or a cavity such as the pouch of Douglas, or an organ and its immediate environment, such as the rectum,
- a particular zone within the anatomical volume itself, the organ, the cavity, the immediate environment of the organ, etc.,
- a planned position of the instrument,
- a particular zone of the surface of the anatomical volume itself, the organ, the cavity, the immediate environment of the organ, or the surface of the skin of the user, a mucous membrane, a zone of the body of the patient that is considered to be malignant or suspicious.

Moreover, if the probe is to be introduced into the body of the patient via an orifice, the orifice can be either natural or artificial.

Optionally, the control unit is configured in such a way as to display the virtual path of the instrument on a two-dimensional image showing a deformation of the instrument.

Optionally, the control unit calculates, from several points of the deformed instrument, a line formed by the deformed instrument, the control unit being configured to use this line in order to estimate the virtual path of the instrument.

Optionally, the control unit activates an alarm when the distance exceeds a given threshold.

Optionally, the control unit displays on the screen a message for activating the alarm.

Optionally, at least the three-dimensional image or two-dimensional image is refreshed automatically.

Optionally, the virtual path is updated automatically and/or the distance between said virtual path and the target is updated automatically.

In particular, the instrument is carried by the monitoring appliance.

In particular, the instrument has a biopsy needle guided by a needle holder of the monitoring appliance.

In particular, the device has at least two instruments, the device being configured in such a way that the control unit generates on the screen:

- a first two-dimensional image including a point of the first instrument and a second two-dimensional image including a point of the second instrument; and/or
- a two-dimensional image including a point of the first instrument and a point of the second instrument.

In particular, the two-dimensional image showing a deformation of the instrument comprises at least one point of introduction of the instrument into the anatomical volume defined by the three-dimensional image, said point being called the "point of insertion of the instrument".

In particular, the two-dimensional image showing a deformation of the instrument comprises at least one point of the instrument intended to act on the target, said point being called the "useful part of the instrument".

In particular, the control unit is configured to generate on the screen, from said three-dimensional image, at least one two-dimensional image presenting both the point of insertion and the useful part of the instrument.

According to a particular embodiment, the control unit is configured to generate on the screen at least one two-dimensional image, said two-dimensional image being derived from a reduction from the volume image to a plane by calculation of an average or a sum of amplitudes around an axis of the volume image.

In particular, the control unit is arranged in such a way as to steer the probe in order to align a reference position of the probe with that of the instrument.

The invention also relates to a method for guiding a medical instrument using such a device, the method having the steps of:

- moving the probe into proximity with the target,
- moving the instrument to the target,
- displaying on the screen at least the two-dimensional image showing the deformation of the instrument,
- estimating a virtual path of the instrument if its insertion were continued as far as the target,
- deducing therefrom at least one distance between said virtual path and the target.

Other features and advantages of the invention will become clear from reading the following description of particular non-limiting embodiments of the invention.

BRIEF DESCRIPTION OF THE DRAWINGS

In the following description, reference will be made to the attached figures, of which:

FIG. 9a is a partial schematic view of a part of a guiding device according to a third embodiment of the invention, FIGS. 9b to 9d illustrate different two-dimensional planes that can be presented to an operator via the probe of the device illustrated in FIG. 9a, FIG. 10 is a schematic view of a part of a guiding device according to a fourth embodiment of the invention.

DETAILED DESCRIPTION OF THE INVENTION

Figure 1:
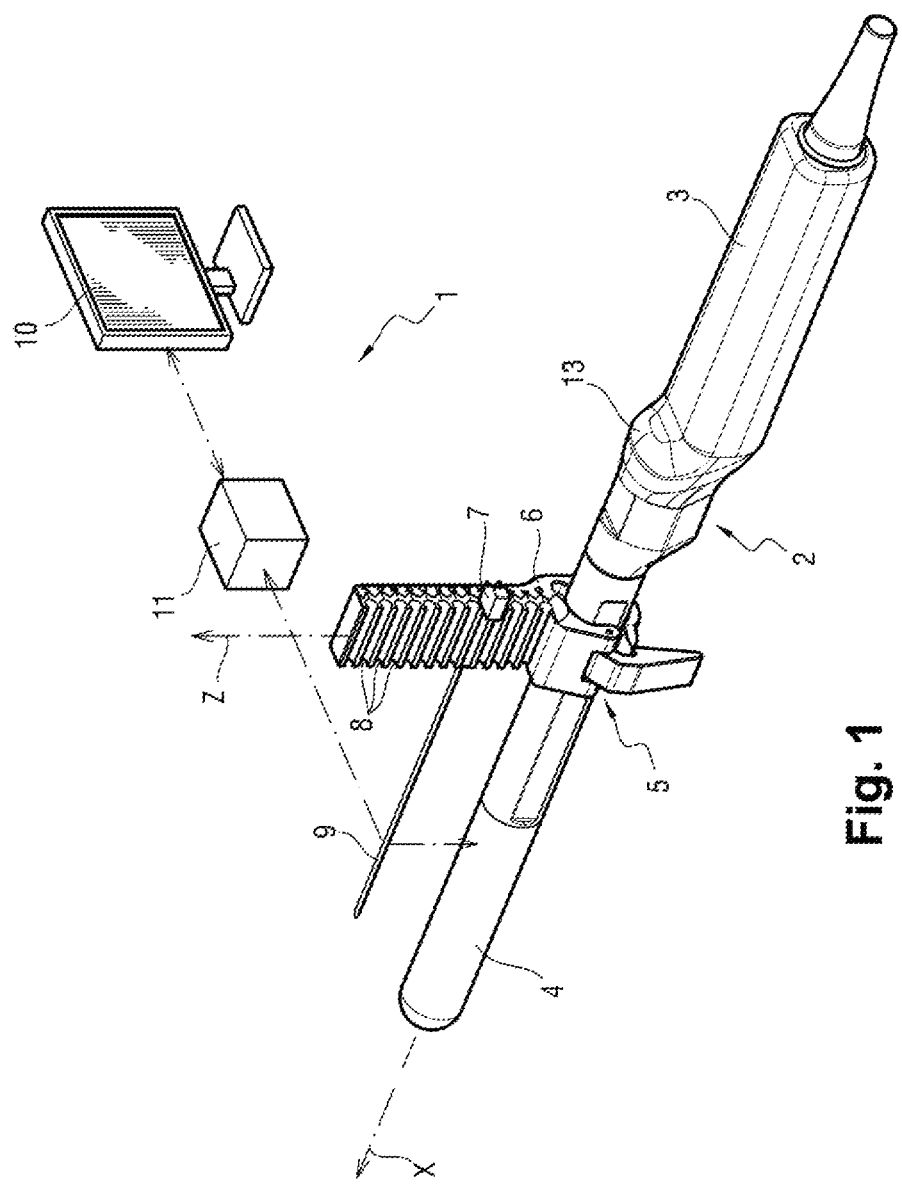
FIG. 1 is a schematic view of a guiding device according to a first embodiment of the invention.
Figure 2:
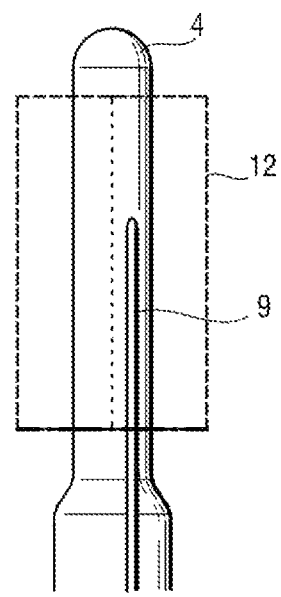
FIG. 2 illustrates in part the appliance illustrated in FIG. 1, FIGS. 3a to 3d illustrate different two-dimensional planes that can be presented to an operator via the probe of the appliance illustrated in FIG. 2, FIG. 4 and FIG. 5a illustrate in part the appliance illustrated in FIG. 1, FIGS. 5b to 5d illustrate different two-dimensional planes that can be presented to an operator via the probe of the appliance illustrated in FIG. 4.

Referring to FIG. 1, the guiding device according to a first embodiment of the invention, generally designated by 1, is here used for a biopsy of the prostate of a patient, specifically by a transperineal approach.

This application is of course not limiting, and it will be possible to use the guiding device 1 for other medical procedures such as ablation and/or for other targets and, for example, other specific zones within other anatomical volumes such as a kidney, a liver, a uterus, etc.

The guiding device 1 has a monitoring appliance 2 extending generally longitudinally along an axis X in order to facilitate its insertion into the rectum of the patient.

Preferably, the appliance 2 has a support 3, which extends parallel to the axis X and which is intended to be grasped at its proximal end by an operator and is continued at its distal end by a shoulder 13 of the appliance 2. Said shoulder is itself continued by a medical imaging probe 4 of the appliance to allow the generation of three-dimensional images of the prostate and its environment, said probe extending along the axis X.

In this way, the appliance 2 is more easily maneuverable by the operator on account of the shoulder 13.

The probe 4 is here an ultrasound probe which is therefore intended to be introduced into the rectum of the patient.

Thus, in the present case, the guiding device 1 according to the particular embodiment of the invention is used for biopsy of the prostate of the patient, by a transperineal approach, and with intrarectal ultrasound imaging.

This application is of course not limiting, and it will be possible to use the guiding device 1 with other types of imaging, i.e. other types of probes. It will thus be possible to use a probe directly generating images, or a probe making it possible to generate images from the information that it transmits. The probe will thus be able to be an ultrasound-type probe. In the same way, the probe can generate two-dimensional images (the guiding device 1 then recreating three-dimensional images from the different two-dimensional images provided by the probe), or the probe can directly generate three-dimensional images. The probe will be able to be motorized or non-motorized. A scan performed by the probe will be effected by a rotation of the probe or by way of various sensors arranged on the probe. For example, the probe will be able to have rows of piezoelectric sensors all extending parallel to one another, the rows being activated one after another in order to obtain two-dimensional images in different orientations.

Thus, the probe 4 here is a probe directly supplying three-dimensional images or a probe 4 providing two-dimensional images whose processing makes it possible to create a three-dimensional image.

The probe 4 here is chosen from among the following probes:
- a probe supplying two-dimensional images and being motorized in order to be able to generate two-dimensional images in different orientations,
- a probe supplying two-dimensional images and comprising sensors arranged at different locations of the probe in order to be able to generate two-dimensional images in different orientations, but without the probe moving, by actuation of various sensors of the probe,
- a probe supplying three-dimensional images by synthesis of two-dimensional images acquired by its one or more sensors (either by motorization of the probe or by way of sensors arranged at different locations of the probe, as proposed above),
- a probe supplying three-dimensional images directly by acquisition of a flow of three-dimensional data.

Preferably, the probe 4 supplies new images automatically at regular intervals, which permits an automatic refresh of the information made available to the operator.

The images are also refreshed either when the probe 4 has performed a complete new scan or during a new scan by the probe 4 (for example, permitting a refresh of the volume image in "slices").

The probe 4 is thus what is called a "four-dimensional" or "4D" probe, because it makes it possible to acquire a flow of volume data that is refreshed in time (the time then forming the fourth dimension).

In all cases, if a scan is necessary in order to be able finally to generate a three-dimensional image, the scanning performed by the probe 4 is either motorized (the probe has a motor) or electronic (by way of various sensors) but is in no case manual (that is to say, it is up to the operator to move the probe manually in order to be able to acquire new two-dimensional images allowing the establishment of a three-dimensional image).

In particular, the probe 4 here is a motorized ultrasound probe. Said probe 4 thus has an ultrasound array for generating two-dimensional images, and a motor arranged in the probe 4 such that a rotation of the motor causes a rotation of the ultrasound array around a longitudinal axis Y of the probe 4. Here, the probe is arranged in the monitoring support in such a way that the axis of rotation of the ultrasound array coincides with the axis X.

When in use, the motor rotates the ultrasound array in a rotation range centered around a reference position of the array (which is also that of the probe 4), such that the array can acquire two-dimensional images on this given angle range, from which images a corresponding volume image is reconstructed. The probe 4 is moreover configured in such a way that the motor can bring the array to a new reference position and/or in such a way that the range of rotation around a given reference position can be modified. The probe 4 is here configured in such a way that the array can perform a continuous scan of + or − X degrees around its reference position, X being between 0 and 90, and preferably between 0 and 85, and chosen depending on the intended application (search for a particular point, a particular section, etc.).

The motor is typically controlled in such a way that the three-dimensional images generated from the data transmitted by the probe 4 are refreshed at a frequency of between 0.1 and 6.5 Hertz, and preferably between 0.2 and 6 Hertz, during a scan by the probe 4. In the specific embodiment of the invention, this makes it possible to display "4D" volume images to the operator, thereby facilitating his work.

The guiding device 1 also has a medical instrument. The instrument has, for example, a biopsy needle 9 which is mounted in a needle holder 5 rigidly connected to the monitoring appliance 2 and here slides in said needle holder 5. In this way, the needle 9 is carried by the monitoring appliance 2 via the needle holder 5 of said monitoring appliance 2. The needle holder 5 is here arranged on the monitoring appliance 2 downstream from the shoulder 13 (in a direction from the support 3 to the probe 4).

In particular, the needle holder 5 has a plate 6 extending along an axis Z substantially perpendicular to the axis X and comprising a plurality of grooves 8 parallel to one another (only one of which is labeled here) and to the axis X. The needle holder 5 also has a stud 7 which can be moved from one groove 8 to another in order to form, with the groove 8 opposite, an orifice through which the needle 9 can be inserted.

The stud 7 facilitates the manipulation of the needle 9, especially by limiting the parasitic movements of the needle 9.

The needle 9 can thus be inserted at a different height into the needle holder 5, which makes it possible to define the height at which the needle 9 will engage in the perineum.

The stud 7 here is of a length shorter than that of a groove and is arranged at the proximal end of the associated groove. Alternatively, the stud 7 is of the same length as the groove.

Preferably, the stud 7 is in a different color from that of the plate 6, in order to make it easier to locate the orifice through which the needle 9 is to be inserted.

Preferably, the plate 6 itself has graphic markers (graduations, alphanumeric characters, etc.) in order to identify the different grooves 8 of the plate 6, i.e. the different levels of the plate 6.

Thus, with the same tool (appliance 2 combined with the instrument 9) and in the same movement, the operator can position the probe 4 in proximity to the prostate, by introducing at least the distal end of the probe 4 into the rectum of the patient, while positioning the needle holder 5 and the associated needle 9 against the perineum in preparation for the upcoming biopsy.

This therefore simplifies the steering of the guiding device 1.

Moreover, the guiding device 1 also comprises a screen 10 and a control unit 11 for controlling the guiding device 1.

The guiding device 1 also has a human-machine interface (not visible here), for example a mouse and/or a keyboard and/or a touch-sensitive panel (possibly coinciding with the screen 10 on which the images are displayed), allowing the operator to interact with the guiding device 1.

Thus, the control unit 11 is connected to the probe 4 and to the screen 10 in order to be able to generate here, on the screen 10, at least one three-dimensional image from data transmitted by the probe 4 (here working in 4D). In the present case, it is therefore the control unit 11 that processes the transmitted two-dimensional images in order to create the corresponding volume image projected on the screen 10. It is also the control unit 11 which here monitors the probe 4 and especially the rotation of the array.

The control unit 11 is furthermore arranged to generate also on the screen 10 at least one two-dimensional image from the data transmitted by the probe 4, without moving the support 3 (for example by working on the basis of the general three-dimensional image generated from the two-dimensional data of the probe 4, or directly on the basis of the two-dimensional data of the probe 4, or by deliberately moving the probe 4 via the motor). As has been indicated above, this image is thus refreshed either when the probe 4 has performed a complete new scan or when the probe 4 has performed a partial new scan.

The control unit 11 is thus able to generate from the data provided by the probe 4, without moving the support 3, and with an automatic refresh, not only a three-dimensional image but also:
- a central 2D image, which image is defined by a central cutting plane in the three-dimensional image comprising the axis X and substantially corresponding to the 2D image acquired by the probe 4 in its reference position, and/or
- a 2D image defined by a plane parallel to that of the central image, and/or
- a 2D image defined by a plane inclined or perpendicular to that of the central image, for example a 2D image called "orthogonal" and normal to the axis X, and/or
- a 2D image defined by a curved surface,
- etc.

Preferably, the control unit 11 is configured in such a way as to symbolize, on the three-dimensional image, the one or more planes, curved surfaces defining the other 2D images also present on the screen 10. For example, the control unit 11 displays on the screen 10 the plane of the central 2D image and simultaneously the three-dimensional image from which said central image is obtained with a representation (for example by a different color) of the plane from which the central image has been generated.

This facilitates the interpretation of the central image by the operator.

According to a particular embodiment, the control unit has a memory for recording different data and in particular different images displayed on the screen 10. These recordings can be automatic and/or controlled by the operator via the human/machine interface.

The data recorded in the memory are, for example, exploited by the device itself or by an external element. For example, although not exclusively, the recorded data are used to modify a map of the biopsies that are to be performed. According to a preferred embodiment, the control unit 11 is configured to automatically optimize the quality of the two-dimensional images displayed on the screen 10. The optimization can be based, for example, on the instrument and/or the target sought and/or potentially a particular zone of the three-dimensional image captured by the operator.

Typically, the control unit 11 adapts at least one of the parameters of the probe 4 and/or one of the parameters of the image (focus, ultrasound frequency, dynamic range, gain, brightness, contrast, etc., for example) in order to optimize the quality of the images projected on the screen 10.

The control unit can be arranged to optimize the quality of each image individually and/or to optimize different images in a global manner.

In order to facilitate the guiding of the instrument, the control unit 11 is furthermore configured in such a way as to project on the screen 10 at least one two-dimensional image comprising here at least one point of the instrument, which image is therefore regularly and automatically refreshed.

With reference to FIGS. 2 and 3*a* to 3*d*, and according to a particular implementation, the point is the point of insertion of the needle 9 into the anatomical volume defined by the three-dimensional image. Said point of insertion is situated generally (both not exclusively) in an internal volume located between the perineum and the prostate of the patient, which internal volume is therefore in the immediate environment of the prostate. The point of insertion of the needle 9 is thus the point of introduction of the needle 9 into the anatomical volume (i.e. a point of intersection between the needle 9 and a proximal zone of the anatomical volume).

Before the insertion of the needle, the control unit 11 monitors the probe 4 such that its reference position is centered relative to the needle holder 5. In this way, the point of insertion of the needle 9 will be present on the central 2D image projected on the screen 10 (defined by a cutting plane then passing through the axes X and Z). The control unit 11 then orders the scanning by the probe 4 around the reference position and the axis X. The space covered by the probe 4 is here symbolized by broken lines in FIG. 2 and labeled 12. The operator then inserts the needle 9 into the perineum. The needle 9 then appears in the three-dimensional volume image.

If the needle 9 extends correctly in the plane of the plate 6 of the needle holder 5, the control unit 11 then displays on the screen 10 the central 2D image which will thus comprise the insertion point of the needle 9. For this purpose, the control unit 11 directly retrieves said central 2D image of the probe 4. Thus, on the screen 10, a new 2D image is displayed that provides information important to the user.

Figure 3A:

However, if the needle 9 has finally become offset with respect to said plane of the plate 6, the central image thus shows neither the point of insertion of the needle 9 nor even the needle 9 (see FIG. 3*a* showing the central image).

In this case, either automatically or following a request by the operator via the human-machine interface, the control unit 11 generates from the volume image a proximal 2D image, also called orthogonal, defined by a sectional plane of the volume image which is normal to the axis X and which passes through a border of the anatomical volume defined by the three-dimensional image.

Figure 3B:
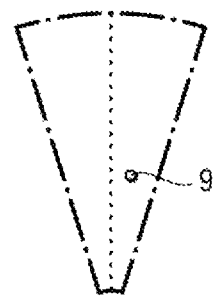

This proximal 2D image is optionally displayed on the screen 10 for the operator. As is illustrated in FIG. 3b (representing the proximal image), this proximal 2D image effectively comprises the insertion point.

Figure 3C:
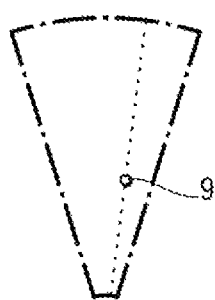
Figure 3D:
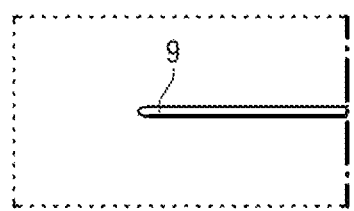
Figure 4:
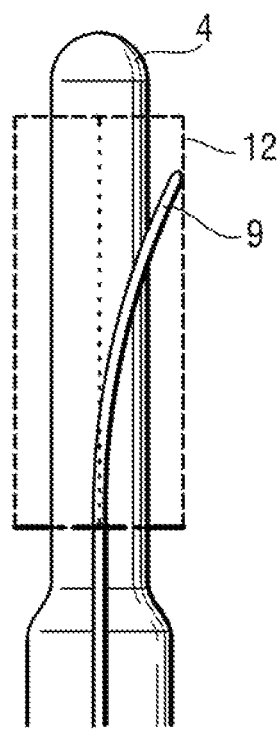

Preferably, either automatically or at the request of the operator, the control unit 11 generates on the screen 10 at least one new 2D image comprising the insertion point. This new 2D image is for example:
- a 2D image parallel to the central 2D image and therefore including the point of insertion (the control unit 11 extracts said image from the volume image),
- a 2D image oblique with respect to the central 2D image and comprising the axis X and the point of insertion (the control unit 11 extracts said image from the volume image),
- a new central 2D image including the point of insertion as illustrated in FIG. 3d, which represents said new image (the control unit 11 then requiring a rotation of the probe 4 in order to align the reference position of the probe 4 with the needle 9, as is shown in FIG. 3c; the control unit 11 identifying the needle 9 by image processing, and causing a displacement of the probe 4 by means of determination of the position of the needle 9 with respect to the probe 4, which image can thus be directly generated by the probe 4 without going through the volume image). Alternatively, if the probe 4 is not motorized but permits electronic scanning, it is possible to ensure the generation of this new central image by activating other sensors of the probe (electronic scanning, no longer motorized).

Thus, the screen 10 displays at least one image comprising the point of insertion of the needle 9, which makes it possible to facilitate the guiding of the needle 9. Of course, several aforementioned images can be displayed simultaneously on the screen 10.

This makes it possible to visualize another part of the body of the patient and of the instrument without having to move the support 3.

Advantageously, these different images are refreshed automatically here.

Typically, during the scanning of the probe 4 in search of the point of insertion, the array performs a continuous scan of + or − A degrees around its reference position, A being between 5 and 15, preferably substantially 10. The speed of rotation is thus defined around substantially 60 degrees per second.

The displayed images are then refreshed automatically at a frequency of substantially 6 Hertz, which makes it possible to work in 4D. It will be noted that the two-dimensional images and the volume image are refreshed at the same frequency, the volume image being refreshed in both directions of rotation of the motor.

Preferably, independently of the images displayed, once the point of insertion has been identified, the control unit 11 causes the probe 4 to align the reference position of the probe 4 with the point of insertion of the needle 9 and reduces the amplitude of the scanning of the probe 4 in order to re-center the scanning of the probe 4 at the working zone on the prostate, thus ensuring a more regular refresh of the different images.

According to a particular embodiment, if the operator no longer needs a refresh of the volume image, the scanning by the probe 4 is temporarily stopped. In this case, the probe 4 acquires only the central 2D image (this happens automatically without having to go through the three-dimensional image), but at a higher frequency, ensuring a more regular refresh of the image. Said frequency is greater than 15 Hertz. Typically, this image is refreshed at a frequency of substantially 20 Hertz. The work thus again entails an automatic refresh, but only at the level of the central 2D image.

In particular, one or more parameters and/or an image are recorded in the memory such that the point of insertion and/or the orientation of the needle 9 can be recorded. These data are then used, for example, to display a position taking into account these different data in the mapping of the biopsy or treatment.

With reference to FIGS. 4 and 5a to 5d, and according to a particular implementation, the point is the useful part of the instrument (that is to say the part of the instrument intended to act on the prostate). In the present case, the useful part is the free end of the needle 9 (i.e. the end intended to perform the biopsy).

The control unit 11 monitors the probe 4 such that the reference position thereof is centered relative to the needle holder 5 (or, as indicated as an option in the first embodiment, such that its reference position is centered relative to the point of insertion of the needle 9). In this way, the supposed free end of the needle 9 in the prostate will be present on the central 2D image projected on the screen 10. The control unit 11 then orders the scanning by the probe 4 around the reference position and the axis X. The space 12 thus covered by the probe 4 is here symbolized by broken lines in FIG. 4.

If the needle 9 extends correctly into the prostate in the plane of the central 2D image, the control unit 11 then displays on the screen 10 said central 2D image, which will thus comprise the free end of the needle 9. For this purpose, the control unit 11 directly retrieves said central 2D image of the probe 4. A new 2D image providing information important to the user is thus displayed on the screen 10.

However, if the needle 9 has finally become offset with respect to said plane, the central image does not then show the free end of the needle 9, as visible in FIG. 5b. In particular, the needle 9 is easily deformable by its shape. The deformations of the needle 9 may be undesirable, but they may also be desired and controlled. Indeed, new techniques make it possible to exploit the deformation of the needles in order to access otherwise inaccessible zones by bypassing obstacles. Nevertheless, in all cases, the deformation of the needle 9 causes non-visualization of the free end of the needle 9 on the central image.

In this case, either automatically or following a request by the operator via the human-machine interface, the control unit 11 generates on the screen 10 at least one new 2D image comprising the free end of the needle 9. This new 2D image is for example:
- an oblique 2D image, as illustrated in FIG. 5d, defined by a cutting plane oblique or orthogonal to the plane defining the central image, said plane comprising the free end of the needle 9 (the control unit extracts said 2D image from the volume image) and preferably being parallel to the axis X,
- an oblique 2D image, defined by the projection of the needle on a cutting plane oblique or orthogonal to the plane defining the central image, said plane comprising the free end of the needle 9 (the control unit extracts said 2D image from the volume image) and preferably being parallel to the axis X, a 2D image, as illustrated in FIG. 5c, derived from a curved surface which follows the deformation of the needle 9 (the control unit 11 extracting said image from the volume image, for example by determination of the curved surface following the deformation of the needle 9 and projection of said curved surface on a plane then defining the image), a 2D image derived from the reduction of the general volume image to a plane (for example the control unit 11 calculates an average, a sum or a maximum amplitude around a given axis according to the position of the needle 9).

The screen 10 thus displays at least one image comprising the free end of the needle 9, which makes it easier to guide the needle 9. Of course, several aforementioned images can be displayed simultaneously on the screen 10.

Advantageously, these different images are here refreshed automatically, which makes it possible to follow the advance of the needle 9 in the patient and thereby simplifies the steering of the needle 9. In particular, the operator can thus very closely follow the passage of the needle 9 into the prostate.

Moreover, this makes it possible to visualize another part of the body of the patient and of the instrument without having to move the support 3. Advantageously, said images here make it possible to visualize the entirety of the needle 9 inserted into the patient, which further facilitates the steering of the instrument. In particular, the point of insertion of the needle 9 can also be visualized here.

It is thus possible to visualize the whole curvature of the needle 9.

Preferably, the control unit 11 records in the memory the curvature of the needle 9 (either the image or coordinate points identifying the curvature of the insertion point and the free end of the needle 9, possibly with intermediate points, etc.). This can subsequently be used to be integrated in the biopsy mapping.

Optionally, independently of the images displayed, once the free end has been identified, the control unit 11 causes the probe 4 to align the reference position of the probe 4 with the free end of the needle 9 and reduces the scanning amplitude of the probe 4 in order to re-center the scanning by the probe 4 at the working zone on the prostate, thus ensuring a more regular refresh of the different images.

According to a particular embodiment, if the operator no longer needs a refresh of the volume image, the scanning by the probe 4 is temporarily stopped. In this case, the probe 4 acquires only the central 2D image (this automatically without having to go through the three-dimensional image), but at a higher frequency ensuring a more regular refresh of the image. Said frequency is greater than 15 Hertz. Typically, this image is refreshed at a frequency of substantially 20 Hertz. The work thus again entails an automatic refresh at the level of the central 2D image.

In particular, one or more parameters and/or an image are recorded in the memory such that the point of insertion and/or the orientation of the needle 9 and/or its deformation can be recorded. These data are then used, for example, to display a position taking into account these different data in the mapping of the biopsy or treatment, or in order to save and indicate the actual values in relation to the theoretical values (i.e. without deformation of the needle 9). This may in future also make it possible to anticipate the deformations expected for the future sampling sites.

Figure 6:
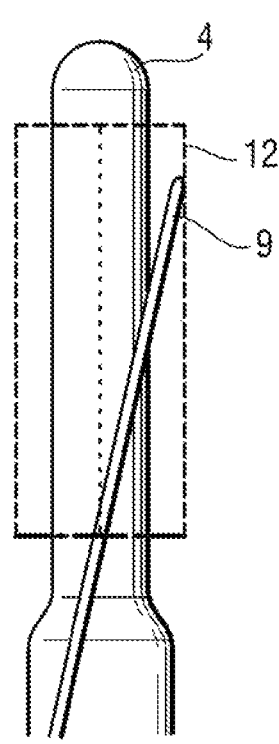
FIG. 6 illustrates in part the appliance illustrated in FIG. 1.

This implementation also applies when the needle is not deformed in a curved manner but instead obliquely, as shown in FIG. 6.

In this case, additionally or alternatively, the control unit 11 can generate on the screen 10 at least one new 2D image coincident with the plane of the needle (the control unit 11 extracting said image from the volume image).

With the guiding device 1 thus described, it is thus possible to detect and follow the insertion of the needle 9 toward a target in the prostate, even in a transperineal approach. In particular, the control unit 11 can permit the insertion of said target (or several targets) into the one or more displayed images. For example, the target is represented by a graphic element (a circle, a sphere, a star, an alphanumeric element) and/or will be in a different color from the rest of the image. This facilitates the work of the operator by making it possible in particular to monitor the distance between needle 9 and target.

In particular, the control unit 11 can permit the insertion of a planned trajectory (i.e. the trajectory that the needle 9 is to follow to reach the target) into the one or more displayed images. For example, the planned trajectory is represented by a particular mark (for example dotted lines) and/or will be in a different color from the rest of the image. This facilitates the work of the operator by making it possible in particular to monitor the distance between needle 9 and target.

This makes it possible to better steer the needle 9 and the medical device 1 in general. In particular, this makes it possible for the operator to better control the position and depth with which he inserts the needle 9 into the prostate.

The target and/or the planned trajectory are for example determined prior to the biopsy, for example at the biopsy planning stage, or are defined at the start of the biopsy after acquisition of first images of the patient and especially of the prostate.

The information transmitted by the probe 4 thus makes it possible to explore the prostate and its immediate environment according to different points of view without moving the appliance 2, or even without moving the reference position of the probe 4, in order to identify the point of insertion, the useful part, the angle of insertion, and also the curvature of the needle 9.

It will be noted that the display of such images would not be available without the guiding device 1, which thus makes it possible to display images in oblique, curved, orthogonal sections, etc.

In addition, the images are refreshed automatically, permitting good monitoring of the needle 9.

Advantageously, the guiding device 1 does not require any particular sensor for generating the two-dimensional images comprising the point of insertion or the useful part of the instrument.

Another implementation of the device will now be described with reference to FIG. 7a.

As has been indicated above, the needle 9 is introduced into the body of the patient with the aid of the images acquired by the probe 4, in particular two-dimensional and/or three-dimensional images.

If the needle 9 reaches the desired target in the prostate (which can be verified, for example, by two-dimensional and/or three-dimensional images of the prostate), the biopsy has been successful and is concluded here.

By contrast, if an undesired deformation of the needle 9 is observed on the images and/or the needle deviates from the planned trajectory, there is a risk of the needle 9 not reaching the target.

The detection of the deformation of the needle 9 can be done manually, by visual detection, or automatically, for example by processing images to compare the planned trajectory with the actual trajectory of the needle 9. Some of the steps that follow for determining the virtual path of the needle 9 can thus be common to the automatic detection of the deformation of the needle 9.

In this case, during a first step 21, the control unit 11 determines the deformation of the needle 9.

Typically, the control unit 11 calculates a three-dimensional line representing the deformed needle 9, according to the following steps:

a) selection of different points of the needle 9 on the volume image and/or two-dimensional images extracted from the volume image (selection made manually by the operator or automatically by the control unit, for example by image processing; the selection will preferably be made from two-dimensional images), and b) interpolation of these different points via a polynomial function, a Bezier curve, a spline function to calculate the three-dimensional line representing the deformed needle 9.

In the points selected at step a, at least the point of insertion of the needle 9 and the point of the free end of the needle 9 are preferably selected. Here, between 3 and 8 additional points on the length of the needle are also selected between these two points.

It will be noted that the three-dimensional line representing the deformed needle 9 has at least one point of the instrument and, in the present case, at least two points (the point of insertion and the point of the free end).

More preferably, the control unit 11 stores in the memory the curvature of the needle 9 (either the image or coordinate points identifying the curvature of the insertion point and free end of the needle 9, possibly with intermediate points, or the three-dimensional line or the two-dimensional line, etc.). This can subsequently be used for a display in the biopsy mapping.

This implementation proves relatively advantageous when the needle 9 is not deformed in a simple manner but in a complex manner, for example to form a sinusoid.

It will also be noted that this is done without having to move the support 3.

During a second step 22, once the control unit 11 has determined the deformation of the needle 9, the control unit estimates a virtual path of the needle 9 if its insertion were continued as far as the target along the actual trajectory. Indeed, by virtue of the three-dimensional line, the control unit 11 knows the position, the orientation and the deformation of the needle between the points indicated. The control unit 11 can easily deduce therefrom how this three-dimensional line continues beyond the point of the free end of the needle 9. According to a particular embodiment, the control unit determines the tangent to this point and deduces therefrom a rectilinear continuation of the three-dimensional line. This can be done, for example, by defining a straight line perpendicular to the tangent and passing through at least two points of the line previously calculated. Said points are preferably the points closest to the useful part of the needle 9.

In this way, the virtual path of the needle 9 is determined.

The control unit here works in the reference frame of the probe.

During a third step 23, the control unit 11 generates on the screen:

a three-dimensional image comprising said virtual path plus the needle 9 and/or the three-dimensional line (which will thus be able to be superposed on the needle 9), and/or a two-dimensional image defined by a coronal plane (i.e. a plane orthogonal to that defining the central 2D image and including the axis X) in the three-dimensional image, the two-dimensional image comprising the projection of the virtual path plus the projection of the needle and/or of the three-dimensional line symbolizing the needle 9 on said coronal plane, said projection thus defining a curved line in two dimensions, and/or an image defined by a plane passing through the three-dimensional line and/or by a plane passing through the virtual path, said image preferably displayed with at least one two-dimensional image alongside in order facilitate the understanding of said image (typically one starts by defining a three-dimensional surface passing through the three-dimensional line and/or the virtual path, which surface is defined by lines all parallel to the axis X, Y or Z and preferably parallel to the axis Z, after which this surface is flattened to obtain a two-dimensional image. For example, the image is defined by a plane passing through the three-dimensional line, then passing through the virtual path, which makes it possible to generate an image containing both the instrument and the virtual path.

For example, the virtual path is represented by a particular line (for example a dotted line) and/or will be in a different color from the rest of the image. This facilitates the work of the operator by making it possible in particular to monitor the distance between needle 9 and target.

Of course, the one or more images displayed can comprise both the virtual path and also the planned trajectory.

This will allow the operator to better represent the situation.

During a fourth step 24, the control unit 11 deduces at least one distance between the virtual path and the desired target.

Preferably, the control unit 11 deduces a minimum distance between the virtual path and the desired target.

For example, the control unit 11 determines a Euclidean distance between each point of the virtual path and each point of the surface of the target and deduces therefrom the shortest distance.

Alternatively, the control unit 11 determines a Euclidean distance between each point of the virtual path and the center of the target and deduces therefrom the shortest distance.

During a fifth step 25, depending on the distance calculated, the control unit 11 indicates whether this distance is acceptable.

Optionally, the control unit 11 indicates if this distance is zero, in other words if the needle 9 will actually reach the desired target despite its deformation.

Figure 7A:
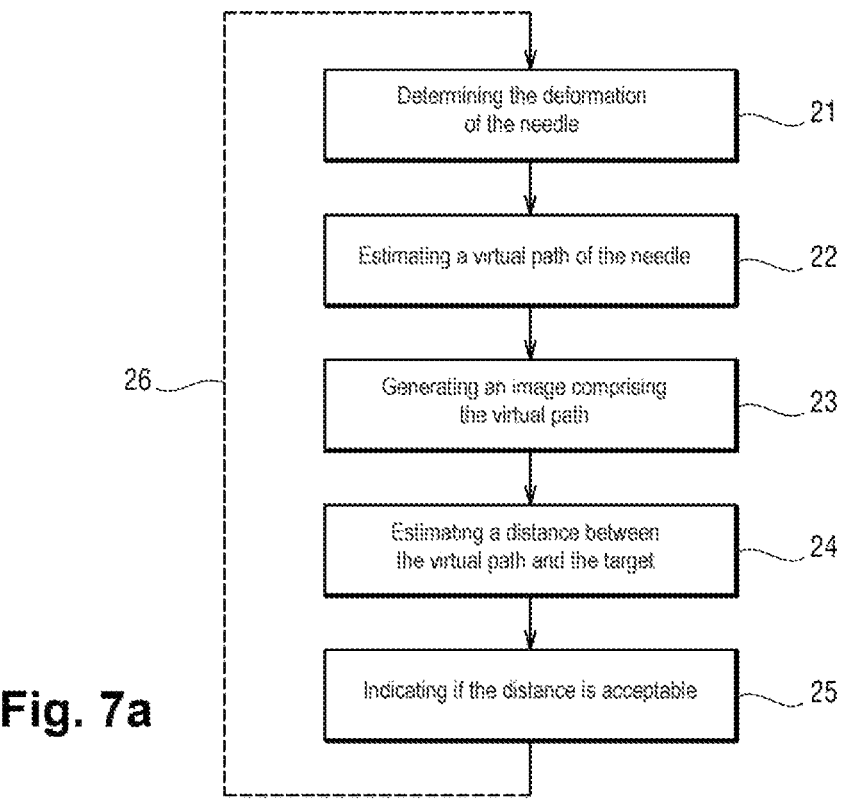
FIG. 7a is a diagram illustrating the different steps in an implementation by the appliance illustrated in FIG. 1, FIGS. 7b and 7c illustrate different two-dimensional planes that can be presented to an operator via the probe of the appliance illustrated in FIG. 4.
Figure 7B:
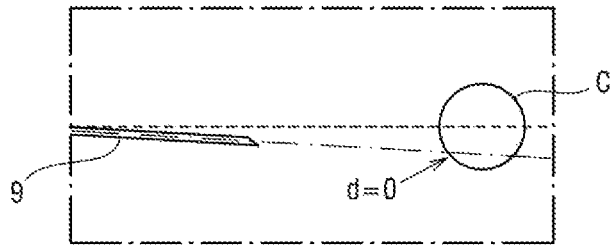
Figure 7C:
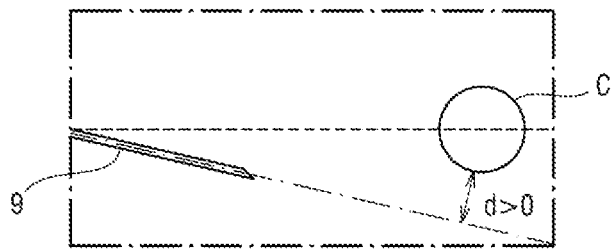

FIG. 7b illustrates a case in which the distance is zero, and FIG. 7c illustrates a case in which the distance is not zero, indicating that the needle 9 will not reach the target C (the broken line representing the planned trajectory, and the dotted line representing the virtual path).

For example, the control unit 11 indicates that this distance is acceptable to the operator via the screen 10, by displaying an alert message of the type with numerical information, binary information of the yes/no type, colored information (for example red/green).

If the distance is acceptable, the operator can thus continue his movement. If not, the operator draws the needle 9 back and starts his maneuver again, in order to reach the desired target, or adjusts the trajectory of the needle 9 if he is able to.

Preferably, working here in 4D, the control unit is configured to display the aforementioned alert message on the screen 10 in such a way that it is updated automatically at the same time as the images (as is indicated schematically by the dotted lines in FIG. 7). It is thus noted that here the virtual path is updated automatically whether in terms of calculation or display on the screen 10. In the same way, the distance between said virtual path and the target is updated automatically.

Thus, the operator is able to continue the maneuver as long as the alert message does not indicate that the estimated distance is unacceptable and that there is a risk of the target not being reached (for example, change of a color indicator from green to red).

Another implementation of the device will now be described.

In this other implementation, the device 1 has, at its human/machine interface, at least one control button for control of the probe 4 by the operator.

Said control button is a button for the angle of rotation of the motor of the probe 4, which allows the operator to be able to control the probe 4 to move to a new reference position. The control button is, for example, a scrolling cursor (physical or virtual, depending on the form of the human/machine interface).

The human/machine interface furthermore comprises here at least one button for controlling the images extracted from the volume image. The human/machine interface here comprises a first control button for controlling the relative angle between a particular two-dimensional image displayed on the screen and the two-dimensional central image corresponding to the reference position of the probe 4. In particular, the human/machine interface here comprises a second control button for controlling the curvature of the particular image (said control button thus making it possible to increase and decrease a radius of curvature of said image, which is plane when the radius of curvature is equal to zero and is a curve of constant curvature when the radius of curvature is not equal to zero). The two control buttons are, for example, scrolling cursors (physical or virtual, depending on the form of the human/machine interface). With the aid of these two control buttons, the operator can thus display on the screen the images of interest without having to move the appliance 2, and the commands that he makes via the two buttons make it possible to control the processing of the volume images acquired by the probe 4.

Typically, the operator can thus browse through the volume image by a succession of two-dimensional images so as to be able to find a two-dimensional image that suits him. The operator can also cause the probe to rotate in order to obtain new and more interesting three-dimensional images.

In particular, the operator (by clicking on the screen 10 or by pressing on the screen 10 if it is touch-sensitive) can select particular points of the image so that the control unit records the coordinates of said points.

Typically, if a two-dimensional image makes it possible to visualize a deformation of the instrument, the operator can select one or more points of the instrument allowing the control unit 11 to record said points representative of the deformation of the instrument and/or to create a three-dimensional line representing the deformed needle 9.

For example, using the control buttons, the operator causes the screen to display different two-dimensional sections until he is able to identify the needle 9 and its deformation. The operator can thus choose a two-dimensional image comprising the free end of the needle 9. The operator then pushes the needle 9 to the desired depth, using said image to guide the needle 9. The operator can then select the free end of the needle 9 and the point of insertion of the needle 9 on the different two-dimensional images (and possibly other points). The control unit 11 then records the various points selected for possible use in the biopsy mapping.

In another example, the operator commands the rotation of the probe in order to select, from the images generated on the screen, the point of insertion, the free end of the needle and, if appropriate, several other intermediate points of the needle. The control unit 11 then generates a three-dimensional line representing the deformed needle 9 and generates one or more images on the screen 10 from said three-dimensional line, as indicated above.

Figure 8:
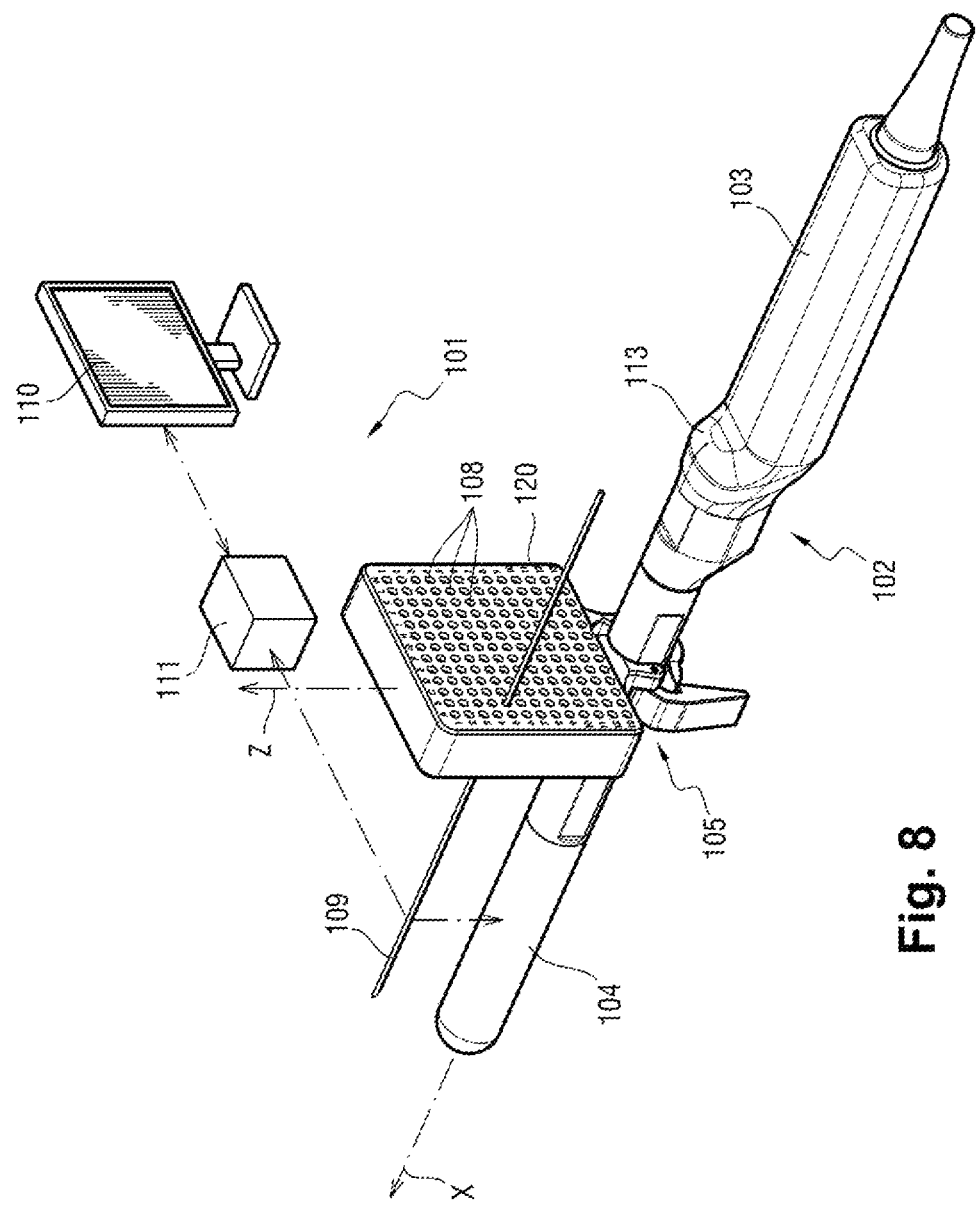
FIG. 8 is a schematic view of a guiding device according to a second embodiment of the invention.

With reference to FIG. 8, a guiding device 100 according to a second embodiment will now be described. This guiding device is here identical to that of the first embodiment, except as regards the needle holder.

Thus, in contrast to the first embodiment, the needle holder 105 comprises a grid 120 which here extends in a plane substantially normal to the axis X. The grid 120 thus comprises orifices 107, all of them parallel to one another and to the axis X. The different orifices 107 are also arranged in columns and in rows on the grid 120 along an axis Y, orthogonal to the axis X, and an axis Z, orthogonal to the axis X and the axis Y.

The needle 109 can thus be inserted at a different height (along the axis Z) in the needle holder 105, which makes it possible to define the height at which the needle 109 will engage in the perineum, but also at a different distance (along the axis Y) in the needle holder 105, which makes it possible to define the distance at which the needle 109 will engage in the perineum.

It is thus possible to guide the needle 109 while having freedom, according to two degrees of freedom, on the zone of insertion of the needle 109 into the perineum.

Preferably, the grid 120 itself comprises graphic markers (graduations, alphanumeric characters, etc.) to identify the different columns of orifices of the grid 120 and different graphic markers to identify the different rows of orifices of the grid 120.

A third embodiment will now be described with reference to FIGS. 9a to 9d.

This guiding device is here identical to that of the first embodiment, except as regards the medical instrument. Indeed, while the device in the first embodiment comprised a single instrument, in the present embodiment the device comprises two instruments.

The first instrument is thus a first biopsy needle 209a and the second instrument is thus a second needle 209b.

The two needles are here mounted in a needle holder identical to that of the second embodiment so as to be able to slide in the needle holder. Alternatively, the two needles will be mounted in the needle holder of the first embodiment.

It is thus possible to guide the two needles 209a, 209b along two degrees of freedom, by virtue of the different orifices of the grid 220, independently of each other.

Thus, with the same tool and in the same movement, the operator can position the probe 204 in proximity to the prostate, introducing at least the distal end of the probe 204 into the rectum of the patient, while positioning the needle holder and the associated needles 209a, 209b against the perineum in preparation for the upcoming biopsy.

As in the first embodiment, the control unit is able, on the basis of the data provided by the probe 204, to create a three-dimensional volume image, then to work on said volume image in order to extract worked two-dimensional images.

Preferably, the following are here displayed on the screen, simultaneously or alternatively:
- a first automatically refreshed two-dimensional image including a point of the first instrument 209a, here the point of introduction into the anatomical volume defined by the three-dimensional image (corresponding to FIG. 9c),
- a second automatically refreshed two-dimensional image including a point of the second instrument 209b, i.e. the point of introduction into the anatomical volume defined by the three-dimensional image (corresponding to FIG. 9d), and
- a third automatically refreshed two-dimensional image including a point of the first instrument 209a or the point of introduction into the anatomical volume defined by the three-dimensional image (corresponding to FIG. 9b).

For example, the first image is derived from a cutting plane inclined with respect to the central cutting plane, the cutting plane thus comprising the axis of the needle 209a; the second image is derived from a cutting plane inclined with respect to the central cutting plane, the cutting plane thus comprising the axis of the needle 209b, and the third image is derived from a cutting plane normal to the axis X and thus comprising the sections of the two needles 209a and 209b.

Of course, other images can be displayed on the screen. For example, the control unit can generate three mutually orthogonal planes for each instrument, making it possible to better appreciate the position of each instrument in space. For example, for each instrument, a first two-dimensional image including the axis of the instrument, a second two-dimensional image normal to said axis, and a third image orthogonal to the first image and to the second image are generated by the control unit.

Of course, it is also possible to display the planned trajectories and/or the virtual paths for one or all of the instruments, as determined with reference to FIGS. 7a to 7c.

Figure 10:
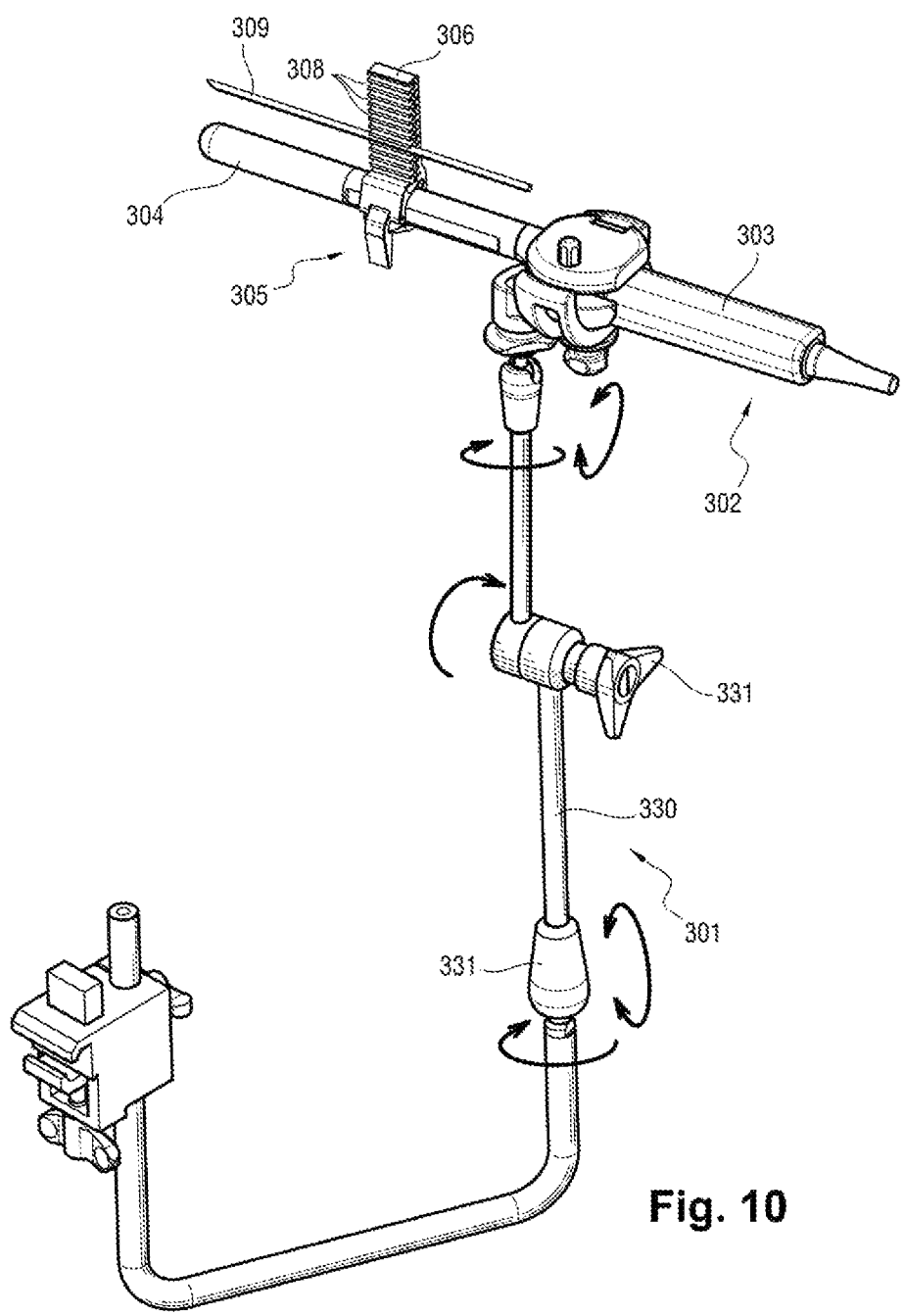

A fourth embodiment will now be described with reference to FIG. 10.

Whereas the guiding device 1 in the first embodiment did not require any particular device for supporting the appliance 2, the guiding device 301 in the present embodiment comprises a robot or an arm associated with the appliance 302.

The guiding device 301 here comprises an arm 330 carrying the appliance 302. Said arm 330 is joined at its other end to a fixed structure (not visible here).

The arm 330 here has means for adjusting the dimensions of the arm 330. For example, the arm 330 comprises wheels 331 for adjusting the height of the arm and the inclination of the appliance 302 relative to the arm 330.

Preferably, the arm 330 is connected to the appliance 302 at the shoulder between the support 303 and the probe 304, which facilitates the manipulation of the appliance 302.

Furthermore, the appliance 302 here is preferably mounted removably on said arm 330, which allows the operator to take it in hand at any time.

Apart from the arm 330, the device according to the fourth embodiment is identical to that of the first embodiment.

Of course, the invention is not limited to the embodiments described, and variants can be made without departing from the scope of the invention as defined by the claims.

In particular, the device will be able to have a different number of instruments and/or have instruments different from those that have been indicated, depending on the intended applications. The instrument will thus be able to change depending on the application for which the device is intended. The instrument may or may not be elongate. Thus, the instrument will be able to be a biopsy instrument, a treatment instrument, a surgical instrument, a needle, an applicator, a fiber, etc. If the device has at least two instruments, the device will thus be able to have at least two cryotherapy applicators, at least two laser fibers, etc.

In the case where the device has several instruments (applicators, needles, etc.), the invention will preferably, although not exclusively, be arranged to be able to generate at least one image per instrument on the screen, such that at least one point of each instrument can be visible simultaneously on the screen if needed. The control unit will then be able to extract, from the data provided by the probe, at least one two-dimensional image associated with each instrument. The control unit will preferably generate two to three mutually orthogonal planes for each instrument, making it possible to better appreciate the position of each instrument in space. For example, for each instrument, a first two-dimensional image will be able to include the axis of the instrument, a second two-dimensional image will be able to be normal to said axis, and a third image will be able to be orthogonal to the first image and to the second image.

The control unit will also be able to generate a two-dimensional image common to both instruments and thus including at least one point of each of the instruments.

Although the three-dimensional image is projected on the screen, the device will be able to be arranged to generate a three-dimensional image but to display on the screen only the two-dimensional images extracted from said three-dimensional image.

The two-dimensional images displayed will make it possible to visualize a temporary deformation of the instrument (as is the case here with the needle) or a permanent deformation (if the instrument is naturally of a non-rectilinear shape, for example).

In the event of significant deformation, the device will be able to use two volume images taken for different reference positions of the probe, so as to obtain a two-dimensional image as an image showing all of the deformation of the instrument.

The various aforementioned implementations and aforementioned embodiments will be able to be combined, partially or entirely.

It will thus be possible to display different combinations of images on the screen other than those indicated, especially although not exclusively according to the desired applications. For example, the display of oblique slices will be relevant in the case of an oblique insertion of the instrument relative to the central image.

The control unit will be able to insert, in the one or more displayed images, a target or targets to be reached in order to perform a medical procedure. For example, the target will be represented by a graphic element (a circle, a sphere, a star, an alphanumeric element) and/or will be in a different color from the rest of the image.

Furthermore, the control unit will be configured to display an image comprising at least the point of the instrument either automatically (for example by image processing for detecting the instrument on the volume image) or at the request of the operator (the operator then giving the order to initiate the automatic detection of the instrument or selecting on the screen, in the volume image, at least the point of the screen for the generation of the new image).

As is indicated in the description, the device will be able to be arranged such that the operator can decide via the human/machine interface what image or images he wishes to see displayed on the screen. In particular, the position and/or the orientation and/or the curvature of the planes and surfaces defining the different images will be, for example, parameters controllable by the operator. In the same way, the operator will be able to optionally order a new position of the probe, by indicating the reference position and/or the amplitude of the scan (electronic or motorized) that he wishes to see applied by the probe.

The control unit will be able to be configured to automatically detect the instrument from the data provided by the probe (for example by processing at least one volume image generated from the data from the probe). The control unit will then be able to be configured to automatically present at least one plane comprising at least one point of the instrument (the most suitable plane for control of the instrument). The control unit will be able to control the probe to define a new scan of the probe to reduce it optimally once at least the point of the instrument is identified. In the same way, the control unit will be able to control the probe to move it and/or modify its reference position and/or modify the sensors in order to have the best possible image of at least the point of the instrument. A reduced volume calculated around an axis of the probe from the volume image will be able to be used by the probe in order to increase the rate of refresh of the images. In general, the control unit will thus be able to be configured to optimize the one or more images generated on the screen.

Although the control unit here displays on the screen a message for activating the alarm if the determined distance exceeds a certain threshold (being above or below this threshold), the control unit will be able to activate any other type of alarm, whether belonging to the device or not, when the distance exceeds a given threshold.

Although the virtual path is determined via a three-dimensional line representing the deformed instrument, it will be possible not to go through this line. It will thus be possible to identify either manually or automatically, on at least one of the images, a point of insertion and/or a point of the useful part of the instrument and/or the angle and/or the deformation of the instrument in order to deduce therefrom the virtual path.

The automatic refresh of the images will be optional.

The invention claimed is:

1. A device for guiding a medical instrument, comprising:
the medical instrument,
a monitoring appliance having a support and a medical imaging probe, which is arranged on the support and which is intended to be positioned in proximity to at least one target present in or on the patient,
a screen, and
a control unit which controls the device and which is connected to the screen and to the probe in order to generate at least one three-dimensional image,
the control unit being configured to generate on the screen, from at least said three-dimensional image, at least one two-dimensional image showing a deformation of the instrument,
the control unit being configured to estimate, from this deformation of the instrument, a virtual path of the instrument if insertion thereof were continued as far as the target, and to deduce therefrom at least one distance between said virtual path and the target,
the control unit calculating, from several points of the deformed instrument that are selected on the three-dimensional image and/or on the two-dimensional image, a line formed by the deformed instrument,
the control unit being configured to use this line in order to estimate the virtual path of the instrument.

2. The device as claimed in claim 1, in which the control unit is configured in such a way as to display the virtual path of the instrument on a two-dimensional image showing a deformation of the instrument.

3. The device as claimed in claim 1, in which the control unit activates an alarm when the distance exceeds a given threshold.

4. The device as claimed in claim 3, in which the control unit displays on the screen a message for activating the alarm.

5. The device as claimed in claim 1, in which at least the three-dimensional or two-dimensional image is refreshed automatically.

6. The device as claimed in claim 1, in which the virtual path is updated automatically and/or the distance between said virtual path and the target is updated automatically.

7. The device as claimed in claim 1, in which the instrument is carried by the monitoring appliance.

8. The device as claimed in claim 1, in which the instrument has a biopsy needle guided by a needle holder of the monitoring appliance.

9. The device as claimed in claim 1, in which the device has at least two instruments, the device being configured in such a way that the control unit generates on the screen:
a first two-dimensional image including a point of the first instrument and a second two-dimensional image including a point of the second instrument; and/or
a two-dimensional image including a point of the first instrument and a point of the second instrument.

10. The device as claimed in claim 1, in which the two-dimensional image showing a deformation of the instrument comprises at least one point of introduction of the instrument into the anatomical volume defined by the three-dimensional image, said point being called the "point of insertion of the instrument".

11. The device as claimed in claim 1, in which the two-dimensional image showing a deformation of the instrument comprises at least one point of the instrument intended to act on the target, said point being called the "useful part of the instrument".

12. The device as claimed in claim 10, in which the control unit is configured to generate on the screen, from said three-dimensional image, at least one two-dimensional image presenting both the point of insertion and the useful part of the instrument.

13. The device as claimed in claim 1, in which the control unit is configured to generate on the screen at least one two-dimensional image, said two-dimensional image being derived from a reduction of the volume image to a plane by calculation of an average or of a sum of amplitudes around an axis of the volume image.

14. The device as claimed in claim 1, in which the control unit is arranged in such a way as to steer the probe in order to align a reference position of the probe with that of the instrument.

15. A method for guiding a medical instrument using a device as claimed in claim 1, the method having the steps of:
moving the probe into proximity with the target,
moving the instrument to the target, displaying on the screen at least the two-dimensional image showing the deformation of the instrument, estimating a virtual path of the instrument if its insertion were continued as far as the target, by calculating, from several points of the deformed instrument that are selected on the three-dimensional image and/or on the two-dimensional image, a line formed by the deformed instrument, and by using this line to estimate the virtual path of the instrument, deducing therefrom at least one distance between said virtual path and the target.

\* \* \* \* \*